United States Patent
Ostermaier

(10) Patent No.: US 9,024,049 B2
(45) Date of Patent: *May 5, 2015

(54) NICKEL COMPOSITIONS FOR PREPARING NICKEL METAL AND NICKEL COMPLEXES

(75) Inventor: John J. Ostermaier, Orange, TX (US)

(73) Assignee: INVISTA North America S.a.r.l., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/821,174

(22) PCT Filed: Jun. 13, 2011

(86) PCT No.: PCT/US2011/040186
§ 371 (c)(1),
(2), (4) Date: Aug. 8, 2013

(87) PCT Pub. No.: WO2012/033555
PCT Pub. Date: Mar. 15, 2012

(65) Prior Publication Data
US 2013/0317242 A1    Nov. 28, 2013

Related U.S. Application Data

(60) Provisional application No. 61/380,445, filed on Sep. 7, 2010.

(30) Foreign Application Priority Data

Dec. 15, 2010    (WO) ................ PCT/US2010/060381

(51) Int. Cl.
*C07F 15/04* (2006.01)

(52) U.S. Cl.
CPC .............. *C07F 15/04* (2013.01); *C07F 15/045* (2013.01)

(58) Field of Classification Search
CPC ..... C07F 15/045; C22B 23/00; C07C 253/10; B01J 31/1845
USPC .............................. 556/13; 558/338; 502/162
See application file for complete search history.

(56) References Cited

U.S. PATENT DOCUMENTS

| | | |
|---|---|---|
| 3,496,215 A | 2/1970 | Drinkard et al. |
| 3,496,217 A | 2/1970 | Drinkard, Jr. |
| 3,631,191 A | 12/1971 | Kane et al. |
| 3,655,723 A | 4/1972 | Drinkard, Jr. |
| 3,672,873 A | 6/1972 | Huggins et al. |
| 3,766,237 A | 10/1973 | Chin |
| 3,816,098 A | 6/1974 | Mackiw et al. |
| 3,846,461 A | 11/1974 | Schook, Jr. |
| 3,847,959 A | 11/1974 | Shock, Jr. et al. |
| 3,903,120 A | 9/1975 | Shook, Jr. et al. |
| 3,914,124 A | 10/1975 | O'Neill et al. |
| 4,045,541 A | 8/1977 | Mercer |
| 4,118,342 A | 10/1978 | Debus et al. |
| 4,416,825 A | 11/1983 | Ostermaier |
| 4,749,801 A | 6/1988 | Beatty et al. |
| 4,946,068 A | 8/1990 | Erickson et al. |
| 5,512,696 A | 4/1996 | Kreutzer et al. |
| 5,688,986 A | 11/1997 | Tam et al. |
| 5,723,641 A | 3/1998 | Tam et al. |
| 5,787,353 A | 7/1998 | Kibbe et al. |
| 5,981,722 A | 11/1999 | Chen et al. |
| 6,069,267 A | 5/2000 | Tam et al. |
| 6,171,996 B1 | 1/2001 | Garner et al. |
| 6,494,931 B1 | 12/2002 | Mukuno et al. |
| 6,906,218 B2 | 6/2005 | Allgeier et al. |
| 7,056,565 B1 | 6/2006 | Cai et al. |
| 7,345,006 B2 | 3/2008 | Bartsch et al. |
| 7,470,805 B2 | 12/2008 | Rosier et al. |
| 7,528,275 B2 | 5/2009 | Bartsch et al. |
| 7,531,682 B2 | 5/2009 | Galland et al. |
| 7,629,484 B2 | 12/2009 | Ritter et al. |
| 7,854,973 B2 | 12/2010 | Dey |
| 8,815,186 B2 | 8/2014 | Ostermaier |
| 2003/0100802 A1 | 5/2003 | Shapiro |
| 2004/0106815 A1 | 6/2004 | Ritter |
| 2006/0107792 A1 | 5/2006 | Collins et al. |
| 2008/0015381 A1 | 1/2008 | Foo et al. |
| 2011/0196168 A1* | 8/2011 | Ostermaier .................. 558/338 |
| 2011/0311428 A1* | 12/2011 | Ostermaier ................ 423/419.1 |

(Continued)

FOREIGN PATENT DOCUMENTS

| | | |
|---|---|---|
| CN | 101478044 A | 7/2009 |
| CN | 101733106 A | 6/2010 |

(Continued)

OTHER PUBLICATIONS

"U.S. Appl. No. 10/993,622, Non-Final Office Action mailed Jul. 8, 2009", 7 pgs.
"U.S. Appl. No. 12/968,341, Final Office Action mailed Nov. 6, 2013", 12 pgs.
"U.S. Appl. No. 12/968,341, Non Final Office Action mailed Mar. 20, 2013", 12 pgs.
"U.S. Appl. No. 12/968,341, Response filed Jan. 13, 2014 to Final Office Action mailed Nov. 6, 2013", 15 pgs.
"U.S. Appl. No. 12/968,373 , Response filed Feb. 11, 2013 to Final Office Action mailed Dec. 17, 2012", 11 pgs.
"U.S. Appl. No. 12/968,373, Final Office Action mailed Dec. 17, 2012", 12 pgs.
"U.S. Appl. No. 12/968,373, Non Final Office Action mailed Oct. 21, 2013", 12 pgs.

(Continued)

*Primary Examiner* — Porfirio Nazario Gonzalez
(74) *Attorney, Agent, or Firm* — Robert B. Furr, Jr.; Nicholas P. Lanzatella

(57) ABSTRACT

Nickel(II) compositions for use in manufacturing nickel metal (Ni(0)) compositions, and specifically to methods of making basic nickel carbonates used to produce nickel metal compositions are disclosed. By varying the molar ratios of carbonates and bicarbonates to nickel salts, the methods provide basic nickel carbonates that produce superior nickel metal-containing solids that are well-suited to forming nickel-ligand complexes with phosphorus-containing ligands. The phosphorus-containing ligands can be monodentate or bidentate phosphorus-containing ligands.

20 Claims, No Drawings

(56) References Cited

U.S. PATENT DOCUMENTS

| | | | |
|---|---|---|---|
| 2013/0143730 | A1 | 6/2013 | Fraga-Dubreuil et al. |
| 2013/0144079 | A1 | 6/2013 | Medhekar et al. |
| 2013/0144082 | A1 | 6/2013 | Fraga-Dubreuil et al. |
| 2013/0345459 | A1* | 12/2013 | Ostermaier ............ 556/13 |

FOREIGN PATENT DOCUMENTS

| | | |
|---|---|---|
| EP | 0114704 A2 | 8/1984 |
| EP | 0673841 A2 | 9/1995 |
| EP | 0985448 A1 | 3/2000 |
| EP | 1724363 A1 | 11/2006 |
| GB | 146407 | 11/1921 |
| GB | 255884 A | 4/1927 |
| GB | 703826 A | 2/1954 |
| GB | 2465467 A | 5/2010 |
| JP | 2001-335326 A | 12/2001 |
| WO | WO-2006/052677 A1 | 5/2006 |
| WO | WO-2007/130206 A1 | 11/2007 |
| WO | WO-2011/075494 A1 | 6/2011 |
| WO | WO-2011/075496 A1 | 6/2011 |
| WO | WO-2011/094411 A1 | 8/2011 |
| WO | WO-2012/170297 A2 | 12/2012 |
| WO | WO-2012/170300 A2 | 12/2012 |
| WO | WO-2012/170537 A2 | 12/2012 |

OTHER PUBLICATIONS

"U.S. Appl. No. 12/968,373, Notice of Allowance mailed Apr. 25, 2014", 7 pgs.

"U.S. Appl. No. 12/968,373, Response filed Dec. 5, 2013 to Non Final Office Action mailed Oct. 21, 2013", 15 pgs.

"U.S. Appl. No. 13/490,116, Final Office Action mailed Apr. 16, 2014", 6 pgs.

"U.S. Appl. No. 13/490,116, Non Final Office Action mailed Feb. 19, 2014", 7 pgs.

"U.S. Appl. No. 13/490,116, Notice of Allowance mailed Jun. 23, 2014", 5 pgs.

"U.S. Appl. No. 13/490,116, Response filed Apr. 9, 2014 to Final Office Action mailed Feb. 19, 2014", 11 pgs.

"U.S. Appl. No. 13/490,116, Response filed Jun. 12, 2014 to Final Office Action mailed Apr. 16, 2014", 10 pgs.

"U.S. Appl. No. 13/490,177, Non Final Office Action mailed Jun. 24, 2014", 7 pgs.

"U.S. Appl. No. 13/490,177, Response filed Apr. 28, 2014 to Restriction Requirement mailed Feb. 28, 2014", 12 pgs.

"U.S. Appl. No. 13/490,177, Response filed Sep. 19, 2014 to Non Final Office Action mailed Jun. 24, 2014", 17 pgs.

"U.S. Appl. No. 13/490,177, Restriction Requirement mailed Feb. 28, 2014", 6 pgs.

"U.S. Appl. No. 13/490,207, Advisory Action mailed Jul. 28, 2014", 3 pgs.

"U.S. Appl. No. 13/490,207, Final Office Action mailed May 19, 2014", 10 pgs.

"U.S. Appl. No. 13/490,207, Non Final Office Action mailed Oct. 22, 2013", 11 pgs.

"U.S. Appl. No. 13/490,207, Response filed Feb. 20, 2014 to Non Final Office Action mailed Oct. 22, 2013", 15 pgs.

"U.S. Appl. No. 13/490,207, Response filed Aug. 19, 2014 to Final Office Action mailed May 19, 2014 and Advisory Action mailed Jul. 28, 2014", 13 pgs.

"U.S. Appl. No. 13/490,207, Restriction Requirement mailed Jun. 14, 2013", 16 pgs.

"Chapter 27—Nickel, Palladium and Platinum", In: Chemistry of the Elements (1st Edition), Greenwood, N. N., et al., Pergamon Press, Oxford, (1984), 1328-1363.

"CN 101478044A, published Jul. 8, 2009—English Translation", 17 pgs.

"English Translation of JP 2001-335326A, published Dec. 4, 2001", 5 pgs.

"International Application Serial No. PCT/US2012/040466, International Preliminary Report on Patentability dated Nov. 14, 2013", 20 pgs.

"International Application Serial No. PCT/US2012/040466, International Search Report mailed Mar. 11, 2013", 11 pgs.

"International Application Serial No. PCT/US2012/040466, Written Opinion mailed Mar. 11, 2013", 21 pgs.

"International Application Serial No. PCT/US2012/041107, International Preliminary Report on Patentability dated Oct. 17, 2013", 28 pgs.

"International Application Serial No. PCT/US2012/041107, International Search Report mailed Mar. 15, 2013", 5 pgs.

"International Application Serial No. PCT/US2012/041107, Response filed Jun. 17, 2013 to Written Opinion mailed Mar. 15, 2013", 9 pgs.

"International Application Serial No. PCT/US2012/041107, Written Opinion mailed Mar. 15, 2013", 14 pgs.

"JP 03-249943A, published Nov. 7, 1991—English Translation", 4 pgs.

"JP 07-005494A, published Jan. 10, 1995—English Translation", 4 pgs.

"JP 2001-335326A, published Dec. 4, 2001—English Translation", 4 pgs.

"Machine translation of JP 2001-335326", [online]. [retrieved on Mar. 11, 2013] Retrieved from the Internet: <http://dossier.ipdl.inpit.go.jp/text_trans.html>, (2013), 9 pgs.

"Sodium carbonate—SIDS Initial Assessment Report for SIAM 15", UNEP Publications, (Oct. 2002), 85 pgs.

Brunauer, S., et al., "Adsorption of Gases in Multimolecular Layers", J. Am. Chem. Soc., 60, (1938), 309-319.

Carlsson, T., et al., "Coprecipitation of Ni with CaCO3: An experimental study", VTT Research Notes 1712, Technical Research Centre of Finland, (1995), 28 pgs.

Carriel, Jonathan T., et al., "Composition of Basic Nickel Carbonates", Journal of the American Chemical Society, 76, (1954), 3839-3843.

Chen, I., et al., "Resistivity to sulfur poisoning of nickel-alumina catalysts", Ind, Eng. Chem. Res., 27(8), (1988), 1391-1396.

Cloutier, L., et al., "The study of the precipitation of carbonates", Proceedings and Transactions of the Royal Society of Canada, 33(III), (1936), 149-164.

Costodes, V. C., et al., "Reactive crystallization of nickel hydroxycarbonate in fluidized-bed reactor: Fines production and column design", Chemical Engineering Science, 61(5), (2006), 1377-1385.

Crosa, M., et al., "Determination of Mean Crystalite Dimensions from X-Ray Diffraction Peak Profiles: A Comparative Analysis of Synthetic Hematites", Clays and Clay Materials, 47(6), (1999), 742-747.

Davidson, J. Michael, et al., "Nucleation Kinetics in the Reactions of Nickel Basic Carbonates with Hydrogen Sulfide: The Carbonate Precipitation Reactions of Divalent Nickel", Industrial & Engineering Chemistry Research, 46(14), (2007), 4772-4777.

Evlash, Yu, et al., "Precipitation of basic nickel carbonate", Zhurnal Prikladnoi Khimii (Sankt-Peterburg, Russian Federation), 58(11), (1985), 2417-2421.

Formanek, Lothar, et al., "Iron, 3. Direct Reduction Processes", In: Ullmann's Encyclopedia of Industrial Chemistry, vol. 19, Wiley-VCH Verlag GmbH & Co., Weinheim, Germany, (2000), 711-726.

Francois-Rossetti, Jeannine, et al., "Structure and constitution of basic nickel carbonates", Journal de Chimie Physique et de Physico-Chimie Biologique, 51, (1954), 451-460.

Gagnon, Paul E., et al., "Contribution to the study of the precipitation of carbonates, borates, silicates and arsenates", Canadian Journal of Research, Section B: Chemical Sciences, 19, B, (1941), 179-204.

Guillard, Damien, et al., "Nickel Carbonate Precipitation in a fluidized-Bed Reactor", Industrial & Engineering Chemistry Research, 40(23), (2001), 5564-5569.

Guillard, Damien, et al., "Optimization of Nickel Hydroxycarbonate Precipitation Using a Laboratory Pellet Reactor", Industrial & Engineering Chemistry Research, 41(13), (2002), 3110-3114.

Guo, Xueyi, et al., "Study on the thermodynamic equilibrium of the complex system of $Ni(II)—NH_3—CO_3^{2-}—H_2O$ and its application to

(56) References Cited

OTHER PUBLICATIONS the precipitation of basic nickel carbonate particles.", *EPD Congress 2004 as held at the 2004 TMS Annual Meeting*, (2004), 443-456.

Guo, Xue-Yi, et al., "Preparation of basic nickel carbonate particles in solution system of Ni(II)—NH$_3$—CO$_3^{2-}$—H$_2$O", *Transactions of the Nonferrous Metals Society of China*, 14(5), (2004), 1006-1011.

Hoffmann, U., et al., "Preliminary results on the behavior of Ni(II) in the calcite-water system", *Mineralogical Magazine*, 62A(Pt. 2), (1998), 642-643.

Ito, Y., et al., "Characterization of a participle size distribution in a Ni—C granular thin film by grazing incidence small-angle x-ray scattering", *Journal of Physics: Conference Series*, vol. 83, (2007), 1-4.

Jaulmes, P., et al., "Solubility and precipitation of slightly soluble salts of weak or moderately strong acids", *Travaux de la Societe de Pharmacie de Montpellier*, 25(2), (1965), 98-110.

Kerfoot, Derek G. E., "Nickel", *In: Ullmann's Encyclopedia of Industrial Chemistry*, Wiley-VCH Verlag GmbH & Co., Weinheim, DE, (2000), 37-101.

Kucha, M. I., "Manufacture of basic nickel carbonate", Issled. i Razrab. Syr'ya dlya Prigot. Katalizatorov, M., *From: Reference Zh., Khim.*, Abstract No. 12L142, (1991), 41-43.

Lascelles, K., "Nickel Compounds", *In: Ullman's Encyclopedia of Industrial Chemistry*, vol. 24, Wiley-VCH Verlag GmbH & Co., Weinheim, Germany, (2005), 117-131.

Lee, Chang-Hwan, et al., "A Study on Nickel Hydroxide Crystallization Characteristics", *Korean Journal of Chemical Engineering* (22(5), (2005), 712-716.

Lewis, A. E., "Fines Formation (and Prevention) in Seeded Precipitation Processes", *KONA*, No. 24, (2006), 119-125.

Li, J., et al., "Formation of Dispersive NiO Nano-particles via Hydrothermal Modification", (English Abstract), *Xiyou Jinshu Cailiao yu Gongcheng (Rare Metal Materials and Engineering*, 33(4), (Apr. 2004), 425-428.

Liu, Fang, et al., "An Improved Purification Method for Preparation of Basic Nickel Carbonate of High Purity via Chemical Precipitation", *Journal of Wuhan University of Technology—Materials Science Edition*, 23(3), (Jun. 2008), 331-333.

Makarov, V. N., et al., "Optimization of Natural Water Purification to Remove Nickel and Copper Ions with Carbonate Flour", *Russian Journal of Applied Chemistry (Translation of Zhurnal Prikladnoi Khimii)*, 74(12), (2001), 2045-2050.

Mallya, R. M., et al., "Studies on the Basic Carbonates of Nickel. Part I: Factors Influencing the Precipitation of Nickel Carbonates", *Journal of the Indian Institute of Science*, 43, (1961), 44-51.

Mallya, R. M., et al., "Studies on the Basic Carbonates of Nickel. Part II: Hydrated Basic Nickel Carbonates", *Journal of the Indian Institute of Science*, 43(2), (1961), 65-75.

Mallya, R. M., et al., "Studies on the Basic Carbonates of Nickel. Part III: Potentiometric Study of Precipitation", *Journal of the Indian Institute of Science*, 43, (1961), 76-86.

Mallya, R. M., et al., "Studies on the Basic Carbonates of Nickel. Part IV: Preparation of Basic Nickel Carbonate and their Differential Thermal Analysis", *Journal of the Indian Institute of Science*, 43, (1961), 87-96.

Mallya, R. M., et al., "Studies on the Basic Carbonates of Nickel. Part V: Thermogravimetric Behavior of Basic Nickel Carbonates", *Journal of the Indian Institute of Science*, 43(3), (1961), 131-40.

Mallya, R. M., et al., "Studies on the Basic Carbonates of Nickel. Part VI: Thermal Decomposition of Basic Nickel Carbonates in Vacuum and the nature of the surfaces", *Journal of the Indian Institute of Science*, 43(3), (1961), 141-147.

Mallya, R. M., et al., "Studies on the Basic Carbonates of Nickel. Part VII: Formation and Configurations of Basic Nickel Carbonates", *Journal of the Indian Institute of Science*, 43(3), (1961), 148-157.

Minkova, N., et al., "Precipitation processes in obtaining basic nickel(II) carbonate and coprecipitation of other basic nickel salts. I. Preparation of basic nickel carbonate free of sulfate ions", *Izvestiya po Khimiya*, 13(2), (1980), 222-228.

Minkova, N., et al., "Precipitation processes in obtaining nickel(II) hydroxocarbonate and co-precipitation of other nickel hydroxo salts. II. Influence of the conditions for obtaining nickel(II) hydroxocarbonate on the amount of co-precipitated sulfate ions", *Izvestiya po Khimiya*, 16(4), (1983), 432-435.

Mittemeijer, E. J., et al., "The "state of the art" of the diffraction analysis of crystallite size and strain", *Zeitschrift für Kristallographie—Crystalline Materials*, 223(9), (2008), 552-560.

Nassler, J., "A new type of basic nickel(II) carbonate", *Collection of Czechoslovak Chemical Communications*, 29(1), (1964), 168-173.

Nitta, Y., et al., "Preparation Chemistry of Precipitated Ni—SiO$_2$ Catalysts for Enantioselective Hydrogenation", *Journal of Catalysis*, 96(2), (1985), 429-438.

Nordhei, C., et al., "Nanophase cobalt, nickel and zinc ferrites: synchrotron XAS study on the crystallite size dependence of metal distribution", *Phys. Chem. Chem. Phys.*, 10, (2008), 1053-1066.

Ozheredova, M. A., et al., "Nickel-containing rinsing waters. Effect of additives and the nature of the precipitant on the degree of treatment", *Khimichna Promislovist Ukraini* (Kiev, Ukraine), (3), (2005), 41-43.

Packter, A., et al., "Precipitation of basic nickel carbonate powders from aqueous solution. Crystallite numbers, composition, and final sizes", *Kristall und Technik*, 10(9), (1975), 985-994.

Pistorius, C. W., "High-Pressure Preparation and Structure of Crystalline Nickelous Carbonate", *Experientia*, 15, (1959), 328-329.

Queneauc, P., et al., "Part II—The Inco Pressure Carbonyl (IPC) process", *J. of Metals*, 21, (1969), 41-45.

Rhamdhani, M. A., et al., "Basic Nickel Carbonate: Part I. Microstructure and Phase Changes during Oxidation and Reduction Processes", *Metallurgical and Materials Transactions B*, 39(2), (2008), 218-233.

Rhamdhani, M. A., et al., "Basic Nickel Carbonate: Part II. Microstructure Evolution during Industrial Nickel Production from Basic Nickel Carbonate", *Metallurgical & Materials Transactions B*, 39(2), (2008), 234-245.

Richardson, Y., et al., "In situ generation of Ni metal nanoparticles as catalyst for H$_2$-rich syngas production from biomass gasification", *Applied Catalysis A: General*, 382(2), (2010), 220-230.

Scardi, P., "Chapter 13. Microstructural Properties: Lattice Defects and Domain Size Efffects", *In: Powder Diffraction Theory and Practice*, Dinnebier, R. E., et al., Editors, RSC, Cambridge, (2008), 376-413.

Sergeev, M., "The influence of temperature on the precipitation of nickel carbonate", *Masloboino-Zhirovoe Delo*, (No. 11), (1928), p. 15.

Taylor, N. J., et al., "Synthesis and Crystal Structure of the Novel Cyclometallophosphine Complex Re$_4$Cl$_2$ (CO)$_{15}$-{MePP(Me)PMe}", *Journal of the Chemical Society, Chemical Communications*, 8, (1985), 476-477.

Teixeira, A. C. S.C., et al., "Deactivation of steam reforming catalysts by sintering: experiments and simulation", *Chemical Engineering Science*, 54(15-16), (1999), 3609-3618.

Tolman, C. A., et al., "Homogeneous Nickel-Catalyzed Olefin Hydrocyanation", *Advances in Catalysis*, 33, (1985), 1-46.

Ueno, Seiichi, et al., "Influence of the conditions of precipitation on the activity of nickel catalysts. II. Precipitation with sodium carbonate", *Kogyo Kagaku Zasshi*, 46, (1943), 45-47.

Ungar, T., et al., "Crystallite size distribution and dislocation structure determined by diffraction profile analysis: princiiples and practical application to cubic and hexagonal crystals", *Journal of Applied Crystallography*, 34(3), (2001), 298-310.

Van Weert, G., et al., "The production of nickel carbonate spheroids from dilute solutions in a pellet reactor.", *Conference: Extractive Metallurgy of Copper, Nickel and Cobalt*. vol. I: Fundamental Aspects, Denver, Colorado, USA, Feb. 21-25, 1993, (1993), 1133-1144.

Vasserman, I. M., et al., "Continuous method for the precipitation of basic nickel carbonate by an automated process", *Tsvetnye Metally* (Moscow, Russian Federation), 37(12), (1964), 25-31.

(56) References Cited

OTHER PUBLICATIONS

Vasserman, I. M., et al., "Separation of substances from solutions by chemical precipitation. III. Automatic control of the process of precipitation of basic nickel carbonate in the system Ni $(NO_3)_2$—$Na_2CO_3$—$H_2O$ by the pH of the solution", *Kh. Z. Branina. Zhur. Priklad. Khim.*, 32, (1959), 2619-2624.

Xiang, L., et al., "Experimental study on synthesis of NiO nanoparticles", *Scripta Materials*, 47, (2002), 219-224.

Zhou, Ping, et al., "Study of a Novel Process for Removal of Heavy Metals from Industrial Wastewater", (English Abstract), *Zhongguo Jishui Paishui*, 14(4), (1998), 17-20.

\* cited by examiner

NICKEL COMPOSITIONS FOR PREPARING NICKEL METAL AND NICKEL COMPLEXES

CROSS REFERENCE TO RELATED APPLICATIONS

This application is a U.S. National Stage Filing under 35 U.S.C. § 371 from International Application No. PCT/US2011/040186. filed on 13 Jun. 2011, and published as WO/2012/033555, on 15 Mar. 2012. which application claims the benefit of the filing dates of U.S. Provisional Application No. 61/380,445 filed on Sep. 7, 2010, and PCT/US2010/060381 filed Dec. 15, 2010, each of which is specifically incorporated herein by reference in its entirety.

FIELD OF THE INVENTION

The invention relates to nickel(II) compositions for use in manufacturing nickel metal (Ni(0)) compositions, and specifically to methods of making basic nickel carbonates (BNC) used to produce nickel metal compositions. The nickel metal compositions can be used to produce zero-valent nickel catalyst complexes with phosphorus-containing ligands.

BACKGROUND OF THE TECHNOLOGY

Hydrocyanation catalyst systems, particularly pertaining to the hydrocyanation of ethylenically unsaturated compounds, are known in the art. For example, systems useful for the hydrocyanation of 1,3-butadiene (BD) to form pentenenitrile (PN) and systems for the subsequent hydrocyanation of pentenenitrile to form adiponitrile (ADN) are known in the commercially important nylon synthesis field.

The hydrocyanation of ethylenically unsaturated compounds using transition metal complexes with monodentate phosphite ligands is documented in the prior art. See, for example, U.S. Pat. Nos. 3,496,215; 3,631,191; 3,655,723 and 3,766,237, and Tolman et al., *Advances in Catalysis,* 1985, 33, 1. The hydrocyanation of activated ethylenically unsaturated compounds, such as with conjugated ethylenically unsaturated compounds (e.g., BD and styrene), and strained ethylenically unsaturated compounds (e.g., norbornene) proceeds without the use of a Lewis acid promoter, while hydrocyanation of unactivated ethylenically unsaturated compounds, such as 1-octene and 3-pentenenitrile (3PN), requires the use of a Lewis acid promoter. Recently, catalyst compositions and processes for the hydrocyanation of monoethylenically unsaturated compounds using zero-valent nickel and bidentate phosphite ligands in the presence of Lewis acid promoters have been described; for example in U.S. Pat. Nos. 5,512,696; 5,723,641 and 6,171,996.

U.S. Pat. No. 3,903,120 describes the preparation of zero valent nickel complexes of the types $Ni(MZ_3)_4$ and $Ni(MZ_3)_2$A; wherein M is P, As or Sb; Z is R or OR, wherein R is an alkyl or aryl radical having up to 18 carbon atoms and can be the same or different, and at least one Z is OR; A is a monoolefinic compound having 2 to 20 carbon atoms; the R radicals of a given $MZ_3$ of $Ni(MZ_3)_2$A preferably being so chosen that the ligand has a cone angle of at least 130°; are prepared by reacting elemental nickel with the monodentate $MZ_3$ ligand at a temperature in the range of 0° C.-150° C. in the presence of a halogen-containing derivative of the monodentate $MZ_3$ ligand as a catalyst. A more rapid reaction is realized by carrying out the preparation in an organonitrile solvent.

U.S. Pat. No. 4,416,825 also describes an improved, continuous process for the preparation of hydrocyanation catalysts including zero valent nickel complexes with monodentate organophosphorus compounds (ligands) by controlling the temperature of the reaction relative to the amount of monodentate ligand and conducting the reaction in the presence of a chlorine ion and organic nitrile such as adiponitrile.

There are several processes that can be used to make nickel catalyst complexes with phosphorus-containing ligands. One method is a reaction between nickel bis(1,5-cyclooctadiene) [$NI(COD)_2$] and a phosphite ligand; however, this process is not very economical because of the high costs of $Ni(COD)_2$. Another process involves the in situ reduction of anhydrous nickel chloride with zinc dust in the presence of the phosphite ligand. For this reaction to be successful, the nickel metal must react with the phosphorus-containing ligand at a sufficient rate to produce the nickel complex.

U.S. Pat. No. 6,171,996 describes zero-valent nickel complexes including bidentate phosphite ligands prepared or generated according to techniques well known in the art, as described, for example, in U.S. Pat. Nos. 3,496,217; 3,631, 191; 3,846,461; 3,847,959 and 3,903,120. For example, divalent nickel compounds can be combined with a reducing agent, to serve as a source of zero-valent nickel in the reaction. Suitable divalent nickel compounds are said to include compounds of the formula $NiY_2$ where Y is halide, carboxylate, or acetylacetonate. Suitable reducing agents are said to include metal borohydrides, metal aluminum hydrides, metal alkyls, Zn, Fe, Al, Na, or $H_2$. Elemental nickel, preferably nickel powder, when combined with a halogenated catalyst, as described in U.S. Pat. No. 3,903,120, is also a suitable source of zero-valent nickel.

In comparison to monodentate phosphorus-containing ligands, bidentate phosphorus-containing ligands generally react more slowly with nickel metals described in the above references. One example of a suitable nickel metal is the INCO type 123 nickel metal powder (Chemical Abstract Service registry number 7440-02-0), derived from the decomposition of nickel carbonyl at elevated temperatures.

Many nickel salts can be converted to nickel metal by reduction with hydrogen at elevated temperatures. Potential sources are nickel oxide, nickel formate, nickel oxalate, nickel hydroxide, nickel carbonate, and basic nickel carbonate (BNC). BNC production has been disclosed by R. M. Mallya, et al. in the *Journal of the Indian Institute of Science* 1961, Vol. 43, pages 44-157 and M. A. Rhamdhani, et al., *Metallurgical and Materials Transactions B* 2008, Vol. 39B, pages 218-233 and 234-245.

SUMMARY OF THE INVENTION

Bidentate ligands can be converted to nickel catalysts that have certain advantages over the nickel catalysts including monodentate ligands, especially as olefin hydrocyanation catalysts. Unfortunately, the INCO type 123 nickel metal powders have insufficient reactivity with the some of these bidentate ligands. Therefore, a nickel metal powder that is sufficiently reactive with bidentate phosphorus ligands and methods of making the nickel metal powder is desirable.

Basic nickel carbonate (BNC) is an inexpensive, commercially available, nickel source. However, evaluation of BNC samples from different mines and chemical vendors has revealed that different available BNC materials give rise to nickel metals with a wide range of reactivity with phosphorus-containing ligands to form nickel complexes.

The invention disclosed herein provides a basic nickel carbonate, which can yield a nickel metal that is highly reactive with both monodentate and bidentate phosphorus-containing ligands in forming nickel metal complexes. Also disclosed are methods of making the basic nickel carbonate, since it has also been discovered that precipitation conditions for making the basic nickel carbonate can influence the activity of the resulting nickel metal. The resulting nickel metal is useful in forming nickel metal complexes for producing pentenenitriles and dinitriles by hydrocyanation.

In one aspect, a method of making a nickel-containing composition is disclosed, including: (i) contacting a precipitant solution with a nickel solution to form a reaction mixture; and (ii) precipitating a nickel(II) composition from said reaction mixture; wherein said nickel solution includes nickel(II) ions and water and said precipitant solution is selected from the group consisting of: (a) bicarbonate ions and water, (b) carbonate ions and water, and (c) mixtures thereof; and further wherein the mole ratio of bicarbonate ions to nickel ions in the reaction mixture is between about 0:1 to about 2:1 and said mole ratio of carbonate ions to nickel ions in the reaction mixture is between about 0:1 to about 1.6:1.

In a further aspect, the precipitant solution is added to the nickel solution, for example, by gradual addition.

Another aspect of the invention is a method of making a nickel complex of a phosphorus-containing ligand by a method that includes reacting nickel metal with a phosphorus-containing ligand wherein the nickel metal is provided by reducing a nickel(II) composition formed according to a process including the steps of:

(i) contacting, while agitating, a nickel(II) salt dissolved in water with a precipitant selected from the group consisting of bicarbonate salt, carbonate salt, and a combination thereof, to form a reaction mixture including an water phase and a precipitate including the nickel(II) composition; and (ii) controlling the contacting rate so that the water phase has a pH between about 4.0 and about 7.5.

The carbon to nickel mole ratio for the nickel(II) composition so formed can vary. In some embodiments, the carbon to nickel mole ratio for the nickel(II) composition is between about 0 and about 0.5.

The controlling step can further include controlling an amount of the precipitant added to the nickel(II) salt dissolved in water (e.g., a type of nickel solution). The amount of precipitant added to the nickel(II) salt dissolved in water varies with the composition of the precipitant.

In some embodiments, the precipitant includes a bicarbonate salt, for example, a bicarbonate salt solution. The contacting rate of a precipitant that includes a bicarbonate salt can be controlled such that a first mole ratio is between about 0.0 and about 2.0, wherein the first mole ratio is the total moles of bicarbonate salt contacted with the nickel(II) salt dissolved in water divided by the total moles of nickel(II) salt in the reaction mixture. For example, the first mole ratio can be between about 1.0 and about 1.9 at a conclusion of contacting the nickel(II) salt dissolved in water with a precipitant.

In some embodiments, the precipitant includes a carbonate salt, for example, a carbonate salt solution. The contacting rate of a precipitant that includes a carbonate salt can be controlled such that a second mole ratio is between about 0.0 and about 1.6, wherein the second mole ratio is the total moles of carbonate salt contacted with the nickel(II) salt dissolved in water divided by the total moles of nickel(II) salt in the reaction mixture. For example, the second mole ratio can be between about 0.8 and about 1.4 at a conclusion of contacting the nickel(II) salt dissolved in water with a precipitant.

In some embodiments, contacting is carried out within a precipitation reactor by feeding a precipitant solution into the precipitation reactor which contains the nickel(II) salt dissolved in water to thereby form the reaction mixture. Feeding of the precipitant solution into the precipitation reactor is controlled, for example:

(a) such that a first mole ratio is between about 0.0 and about 2.0, wherein the first mole ratio is the total moles of bicarbonate salt divided by the total moles of nickel (II) salt charged into the precipitation reactor; or (b) such that a second mole ratio is between about 0.0 and about 1.6, wherein the second mole ratio is the total moles of carbonate salt contacted with the nickel(II) salt dissolved in water divided by the total moles of nickel (II) salt charged into the precipitation reactor.

During the methods described herein for forming nickel(II) composition the reaction mixture temperature can be maintained, for example, between about 25° C. and about 90° C. Carbon dioxide can also be added to the nickel(II) salt dissolved in water or to the reaction mixture.

In some embodiments, the methods described herein can include digesting the precipitate formed by mixing the nickel (II) salt dissolved in water with a precipitant. Digestion can be performed by heating the reaction mixture containing the precipitate, for example, between about 50° C. and about 90° C. for a time period, for example, of about 0.5 hour to about 24 hours.

In some embodiments, particularly when the precipitant includes a bicarbonate salt, precipitating the nickel(II) composition from the reaction mixture can be performed while utilizing at least two precipitating conditions selected from the group consisting of precipitating conditions (1), (2), and (3): (1) a reaction mixture temperature between about 60° C. and about 80° C.; (2) addition of carbon dioxide to the reaction mixture; and (3) a first mole ratio between about 0.0 and about 1.6. In further embodiments, each of conditions (1), (2), and (3) are utilized.

In some embodiments, particularly when the precipitant includes a carbonate salt, precipitating the nickel(II) composition from the reaction mixture can be performed while utilizing at least two precipitating conditions selected from the group consisting of conditions (4), (5), and (6): (4) a reaction mixture temperature between about 60° C. and about 80° C.; (5) addition of carbon dioxide to the reaction mixture; and (6) a second mole ratio between about 0.0 and about 1.2. In further embodiments, conditions (4), (5), and (6) are utilized.

After forming the precipitate, the methods can further include separating the precipitated nickel(II) composition from the reaction mixture followed by at least one processing step selected from the group consisting of:

(a) washing the precipitated nickel(II) composition with water; and (b) at least partially drying the precipitated nickel(II) composition.

For example, at least a portion of the washed precipitated nickel(II) composition from processing step (a), at least a portion of the at least partially dried precipitated nickel(II) composition from processing step (b), or at least a portion of the washed and at least partially dried precipitated nickel(II) composition from processing steps (a) and (b) can be reduced to form the nickel metal.

In some embodiments, the phosphorus-containing ligand for complexing with the nickel metal formed from the nickel (II) composition can be a monodentate phosphite, monodentate phosphonite, monodentate phosphinite, monodentate phosphine, bidentate phosphite, bidentate phosphonite, bidentate phosphinite, bidentate phosphine, mixed bidentate ligand, or any combination thereof; wherein the mixed bidentate ligand is selected from the group consisting of a phosphite-phosphonite, a phosphite-phosphinite, a phosphite-phosphine, a phosphonite-phosphinite, a phosphonite-phosphine, and a phosphinite-phosphine. In some embodiments, the phosphorus-containing ligand is a bidentate phosphite, bidentate phosphonite, bidentate phosphinite, bidentate phosphine, mixed bidentate ligand, or any combination of such members; when such ligands are used to make the nickel complex, the reaction of the nickel metal with the phosphorus-containing ligand further includes a Lewis acid.

Another aspect of the invention is a method to make a nickel complex of a phosphorus-containing ligand, wherein a phosphorus-containing ligand reacts with nickel metal to make the nickel complex of the phosphorus-containing ligand; characterized in that the nickel metal is produced by reducing a nickel(II) composition and the nickel(II) composition produces carbon dioxide when heated. The nickel(II) composition can, for example, be made by any of the methods described herein.

DETAILED DESCRIPTION

Definitions

Monodentate: Each ligand molecule comprises a single phosphorus atom that can bond to a nickel atom to form the nickel complex which can include one or more monodentate ligands.

Bidendate: Each ligand molecule comprises two phosphorus atoms that both can bond to a single nickel atom to form the nickel complex.

Phosphite: An organophosphorus compound including a trivalent phosphorus atom bonded to three oxygen atoms.

Phosphonite: An organophosphorus compound including a trivalent phosphorus atom bonded to two oxygen atoms and one carbon atom.

Phosphinite: An organophosphorus compound including a trivalent phosphorus atom bonded to one oxygen atom and two carbon atoms.

Phosphine: An organophosphorus compounding including a trivalent phosphorus atom bonded to three carbon atoms.

Disclosed are novel nickel(II) compositions, including nickel, and methods of making the same. In some embodiments, the nickel(II) compositions include basic nickel carbonate, also referred to as BNC. BNC, particularly the BNC made as described herein, is a suitable source of Ni(II) for reduction and ligand complexation in the preparation of zero-valent nickel hydrocyanation catalysts, and is sometimes referred to herein as "BNC nickel." In an example, BNC can be described with a chemical formula of $[Ni(CO_3)_x(OH)_y]_z$ $(H_2O)_n$, wherein $x=z-(y/2)$; $y=2z-2x$; $z=1$ to $100$; and $n=0$ to $400$. BNC can be referred to as including nickel(II) ions, carbonate ions, hydroxide ions, and water molecules. In some embodiments, the BNC nickel is synthesized using sources of Ni(II), for example, Ni(II) salts. The BNC nickel can be synthesized using the procedures disclosed herein. Certain forms of BNC nickel, including BNC nickel generated by some of the procedures detailed herein, can yield a Ni(0) that is particularly well-suited to formation of nickel(0) complexes with phosphorus-containing ligands. For example, the Ni(0) metal generated from the BNC made as described herein is particularly well-suited for forming a nickel complex including nickel and at least one phosphorus-containing ligand disclosed herein. For example, Ni(0) that is particularly well-suited to forming such a nickel complex gives higher yields of the nickel complex. Features of Ni(0) that are well-suited to forming a nickel complex include, for example, low carbon content, large surface area, small particle size, small crystallite size (e.g. less than 89 nm), and optionally a broad size distribution. Ni(0) can have a surface area of, for example, about 0.5 square meters per gram, 2 $m^2/g$, 4, 6, 10, 20, 30, 40, about 50 $m^2/g$, or any value in between. In some examples, Ni(0) with a surface area greater than about 2 $m^2/g$, 5 $m^2/g$, 10 $m^2/g$, 20 $m^2/g$ or greater than about 30 $m^2/g$ are particularly well-suited to forming nickel complexes with phosphorus-containing ligands. BNC nickel that has features including, for example, low carbonate content, a molar ratio of $NiCO_3:Ni(OH)_2$ of less than approximately 1, with a mass ratio of Ni:C of at least about 10:1, or any combination thereof, can produce Ni(0) with low levels of carbon impurities, including carbon impurities due to carbonate impurities, and thus produces Ni(0) that is well-suited to nickel-ligand complex formation. The calcination or heating or BNC nickel having features including a low carbonate content, a molar ratio of $NiCO_3:Ni(OH)_2$ of less than approximately 1, with a mass ratio of Ni:C of at least about 10:1, or any combination thereof, more readily produces carbon dioxide ($CO_2$), and thus causes more complete conversion to NiO, with fewer carbon impurities in the NiO, including carbonate impurities. By producing NiO that has a lower carbon content, including a lower carbonate content, an improved NiO product is generated from the BNC where the NiO has fewer carbon impurities.

Therefore, disclosed herein are novel nickel-containing solids including nickel metal, derived from nickel(II) compositions of basic nickel carbonates, and methods of making the same. The nickel(II) compositions of BNCs can be made by contacting a precipitant solution with a nickel solution (for example, in a precipitation reactor) to form a reaction mixture; and (ii) precipitating the nickel(II) composition from the reaction mixture, wherein said nickel solution includes nickel (II) ions and water and said precipitant solution is selected from the group consisting of: (a) bicarbonate ions and water, (b) carbonate ions and water, and (c) mixtures thereof.

The amount precipitant added and the rate of precipitant addition can vary. For example, the mole ratio of bicarbonate ions to nickel ions in the reaction mixture at the conclusion of said feeding can range from 0.5:1 to 2:1, including from about 0.5:1 to about 1.6:1, from about 0.5:1 to about 1.2:1, from about 1.0:0 to about 1.9:1, from about 1.2:1 to about 1.9:1, from about 0.8:1 to about 1.4:1, from about 1:1 to about 1.8:1, from about 1:1 to about 1.6:1, from about 1:1 to about 1.4:1, from about 0.8:1 to about 1.4:1, and from about 0.8:1 to about 1.2:1. The mole ratio of carbonate ions to nickel ions in the reaction mixture at the conclusion of said feeding can range from 0.3:1 to 1.6:1, including from about 0.5:1 to about 1.4:1, from about 1:1 to about 1.2:1, from about 0.8:1 to about 1.4:1, from about 1:1 to about 1.6:1, from about 1.0:1 to about 1.6:1, from about 1.0:1 to about 1.4:1, from about 0.8:1 to about 1.4:1, and from about 0.8:1 to about 1.2:1. Blends of bicarbonates and carbonates can also be used in the precipitant solution. As detailed more fully below, the molar ratio has a surprising effect on the resulting nickel metal's effectiveness of reacting with the phosphorus ligands.

The rate of precipitant addition can vary. The precipitant can be added or fed continuously into the nickel solution (e.g., nickel salts in water). In some embodiments, the precipitant can be added or fed intermittently into the nickel solution. To avoid introducing excess precipitant (e.g., excess bicarbonate or carbonate), the precipitant can be added gradually or intermittently in small amounts.

The precipitation reactor can be any suitable containment vessel such as a tank or pipe. The precipitation can be performed in a batch or continuous fashion. Further, the reaction mixture can be agitated prior to and/or during the precipitation of the nickel(II) composition. For example, agitation can be done by mechanical stirring, pumped circulation loop, flow-through static mixture, or ultrasound. The use of high sheer during precipitation can prevent particle agglomeration and can give smaller resulting BNC nickel particles. Therefore, in some embodiments, the precipitant is added to the nickel solution with high-sheer agitation or stirring. Reactor designs, stirring designs, and the application of high amounts of power to stirring are examples of factors that can cause a high-sheer stirring of the reaction mixture during precipitation.

The nickel(II) composition can be precipitated within a temperature range of from about 0° C. to about 90° C., including from about 20° C. to about 90° C., from about 20° C. to about 70° C., from about 20° C. to about 50° C., from about 50° C. to about 90° C., from about 60° C. to about 80° C., and from about 65° C. to about 75° C. In some embodiments, increased temperature during precipitation can decrease the proportion of carbonate ions in the resulting BNC nickel. Furthermore, the nickel(II) composition can be precipitated from the reaction mixture in the presence of added carbon dioxide. For example, the carbon dioxide can be added to the precipitation reactor, added to the nickel solution, added to the precipitant solution, or added to the reaction mixture, and any combination thereof. Also, the precipitant solution can be fed over a period of from about 30 minutes to about 60 minutes, and can be done in a semi-continuous or continuous manner. Further, the precipitant solution can be added to the nickel solution in the precipitation reactor in a semi-continuous or continuous manner, for example, gradual addition. In some embodiments, the use of a higher pH during precipitation can decrease the proportion of carbonate ions in the resulting BNC nickel precipitate. For example, a pH value of about 4, 5, 6, 7, 8, or about 9, or higher can be used. In one example, the pH increases from about 4.9 to about 5.8 during the precipitation.

The reaction mixture can also be digested after contacting the precipitant solution to the nickel solution by heating the reaction mixture from between about 50° C. and about 90° C. for a period of from about 0.25 hours to about 24 hours. Other suitable temperature ranges include from about 60° C. to about 80° C. and from about 65° C. to about 75° C. Under conditions, longer digestion times can cause larger BNC nickel particles in the resulting precipitate. Other suitable time periods can range from about 0.5 hours to about 20 hours, including from about 0.5 hour to about 14 hours, from about 1 hour to about 12 hours, from about 1 hour to about 8 hours. In some embodiments, the reaction mixture is heater between about 50° C. and about 90° C. for a period of from about 0.25 hours to about 2 or 3 or 4 hours.

The disclosed nickel(II) composition methods can further include, after the precipitation step, washing the precipitated nickel(II) composition with water; and at least partially drying the precipitated nickel(II) composition. For example, the precipitated nickel(II) composition from the reaction mixture is separated from the reaction mixture by filtration or decantation, the resulting precipitated nickel(II) composition is washed with water by filtration or decantation, and the resulting precipitated nickel(II) composition is dried by water evaporation between about 60° C. and about 100° C. Drying can be performed under ambient pressure or under vacuum, and in the presence of an inert gas such as nitrogen. In some embodiments, increased drying times can cause increased proportions of carbonate ions in the resulting BNC nickel, or in a nickel oxide generated from the BNC nickel.

The nickel solution, including nickel(II) ions and water, can be prepared by dissolving a nickel(II) salt in water. The nickel salt can be any salt that is soluble in water, for example $NiCl_2$, $NiSO_4$, and $Ni(NO_3)_2$.

In some embodiments, a precipitant is used to generate a BNC (nickel containing) precipitate. The precipitant includes bicarbonate and/or carbonate ions with counterions of sodium, potassium, or ammonium. The precipitant solution, including bicarbonate ions, can be prepared by dissolving a bicarbonate salt, for example, $NaHCO_3$ and $NH_4HCO_3$, in water. Alternatively, or additionally, the precipitant can be prepared in-situ by dissolving $CO_2$ and an alkali metal hydroxide or ammonia in water by known methods. Likewise, the precipitant solution, including carbonate ions, can be prepared by dissolving a carbonate salt, for example $Na_2CO_3$ or it can be prepared in-situ by dissolving $CO_2$ and an alkali metal hydroxide in water by known methods. The anion of the nickel salt and cation of the bicarbonate or carbonate salt can be selected such that a salt produced from the precipitation, including both the cation and anion from the reaction mixture (for example NaCl), is soluble in the water of the reaction mixture. Such a selection provides a method for separating said salt product from the precipitated nickel(II) composition.

Also disclosed is a method of making a nickel-containing solid including nickel metal. The method includes: (i) providing the nickel(II) compositions disclosed above; and (ii) reducing at least a portion of the nickel(II) composition of step (i) with a reducing agent to form a nickel-containing solid, including nickel metal, wherein said nickel-containing solid is adapted to effectively react with a bidentate phosphorus containing ligand to form a nickel complex of the phosphorus-containing ligand. The nickel-containing solid is more reactive with phosphorus-containing ligands than nickel-containing solids made by other processes, such as INCO type 123 nickel metal powder, nickel oxide, nickel formate, nickel oxalate, nickel hydroxide, nickel carbonate. The high reactivity is partially due to the BNC processes disclosed above, as well as the reducing process. The reducing agent can be hydrogen, carbon dioxide, carbon monoxide, methane, ammonia, hydrogen sulfide, merely to name a few nonlimiting examples of suitable reducing agents.

As previously stated, the amount of bicarbonate or carbonate ions fed relative to the nickel(II) ions charged greatly affects the reactivity of the resulting nickel-containing solid with the phosphorus-containing ligand to make a nickel complex. Because of the high costs of nickel, producers of BNC-type nickel(II) compositions would be led to add excess amounts of the precipitant solution so as to recover as much of the nickel as economically feasible. However, it has been surprisingly found that the use of excess precipitant produces nickel metal of low reactivity for the phosphorus-ligand complex reaction. Thus, in some embodiments, the precipitant is not added in excess, relative to the amount of nickel. Highly reactive nickel is produced when reduced levels of precipitant are used, and presumably more of the nickel(II) ions are allowed to remain dissolved in the water of the resulting reaction mixture.

It has also been found that the precipitated nickel(II) composition made using bicarbonate ions filters and washes much faster than the precipitated nickel(II) composition made using carbonate ions. Also, the filtered precipitated nickel(II) composition made using bicarbonate ions dries to a soft powder with little shrinkage. For these reasons, producing the nickel-containing solid using bicarbonate ions provides further desirable properties for downstream processing and handling of the dried precipitated nickel(II) composition.

The reduction of the nickel(II) composition with a reducing agent to form a nickel metal-containing solid can be performed at a temperature in the range from about 150° C. to about 700° C., including from about 300° C. to about 500° C., and from about 350° C. to about 450° C. In another aspect, the reduction temperature is from about 350° C. to about 1500° C., including from about 350° C. to about 450° C. The reduction pressure can range from about 0.01 atmospheres to about 100 atmospheres. Reduction can be carried out for a period of at least about 30 minutes using a stoichiometric excess of a reducing agent, such as hydrogen, even though one mole of hydrogen per mole of nickel(II) composition to be reduced is the theoretical and stoichiometric amount required for complete reduction. For example, the reducing period can be between about 1 to about 2 hours using a 2:1 mole ratio of hydrogen to moles of nickel atoms in the nickel oxide of the nickel composition.

The disclosed nickel containing solids can be reacted with a phosphorus-containing ligand to make a nickel complex of the phosphorus-containing ligand. Such complexes are useful as a catalyst precursor for at least one of the following reactions: (1) reacting 1,3-butadiene with hydrogen cyanide to produce 2-methyl-3-butenenitrile and 3-pentenenitrile; (2) reacting 2-methyl-3-butenenitrile to produce 3-pentenenitrile; (3) reacting 3-pentenenitrile with hydrogen cyanide in the presence of a Lewis acid to produce adiponitrile; and (4) reaction 2-pentenenitrile with hydrogen cyanide in the presence of a Lewis acid to produce 3-pentenenitrile, 4-pentenenitrile, and adiponitrile.

The phosphorus-containing ligand can be a monodentate phosphite, monodentate phosphonite, monodentate phosphinite, monodentate phosphine, bidentate phosphite, bidentate phosphonite, bidentate phosphinite, or bidentate phosphine, and any combination of these members. Further, the phosphorus-containing ligand can be a monodentate phosphite to form the nickel complex of the monodentate phosphite then the nickel complex of the monodentate phosphite can be combined with a bidentate phosphorus-containing ligand. Likewise, the phosphorus-containing ligand can be a bidentate phosphite further including a monodentate phosphite.

When the phosphorus-containing ligand is a bidentate phosphite, the bidentate phosphite can be selected from the members of the groups consisting of Formula Ia, Formula Ib, Formula Ic, or any combination of these members:

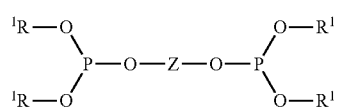

Formula Ia

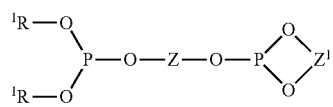

Formula Ib

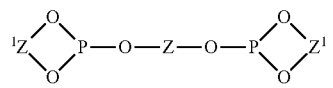

Formula Ic wherein in Formulae Ia, Ib, and Ic, $R^1$ is phenyl, unsubstituted or substituted with one or more $C_1$ to $C_{12}$ alkyl, $C_1$ to $C_{12}$ alkoxy groups, or groups of Formulae A and B, or $-(CH_2)_n OY^2$; or naphthyl, unsubstituted or substituted with one or more $C_1$ to $C_{12}$ alkyl or $C_1$ to $C_{12}$ alkoxy groups, or groups of Formulae A and B, or $-(CH_2)_n OY^2$; or 5,6,7,8-tetrahydro-1-naphthyl;

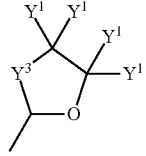

Formula A

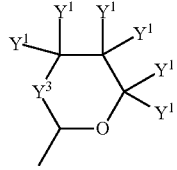

Formula B wherein in Formulae A and B, $Y^1$ is independently selected from the group of H, $C_1$ to $C_{18}$ alkyl, cycloalkyl, or aryl, $Y^2$ is independently selected from the group of $C_1$ to $C_{18}$ alkyl, cycloalkyl, or aryl, $Y^3$ is independently selected from the group of O or $CH_2$, and n=1 to 4;

wherein in Formulae Ia, Ib, and Ic,

O—Z—O and O—$Z^1$—O are independently selected from the group consisting of structural Formulae II, III, IV, V, and VI:

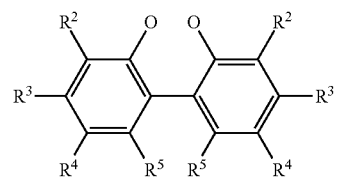

II

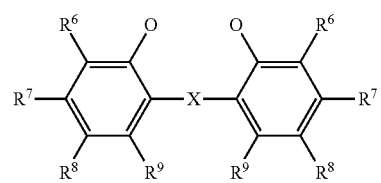

III wherein in Formulae II and III, $R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy; X is O, S, or CH($R^{10}$);

$R^{10}$ is H or $C_1$ to $C_{12}$ alkyl;

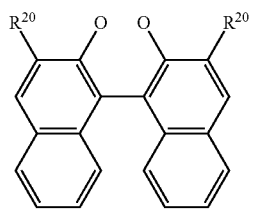

IV

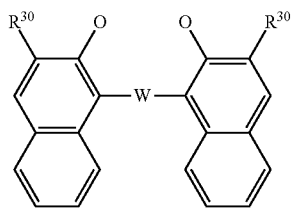

wherein in Formulae IV and V, $R^{20}$ and $R^{30}$ are independently selected from the group consisting of H, $C_1$ to $C_{12}$ alkyl, and $C_1$ to $C_{12}$ alkoxy, and $CO_2R^{13}$;

$R^{13}$ is $C_1$ to $C_{12}$ alkyl or $C_6$ to $C_{10}$ aryl, unsubstituted or substituted with $C_1$ to $C_4$ alkyl;

W is O, S, or $CH(R^{14})$;

$R^{14}$ is H or $C_1$ to $C_{12}$ alkyl;

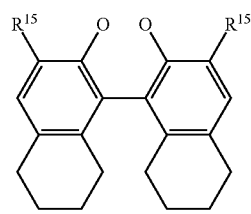

and wherein in Formulae VI, $R^{15}$ is selected from the group consisting of H, $C_1$ to $C_{12}$ alkyl, and $C_1$ to $C_{12}$ alkoxy and $CO_2R^{16}$; $R^{16}$ is $C_1$ to $C_{12}$ alkyl or $C_6$ to $C_{10}$ aryl, unsubstituted or substituted with $C_1$ to $C_4$ alkyl.

When the phosphorus-containing ligand is a bidentate phosphite, the bidentate phosphite can be selected from the group consisting of Formula VII and VIII,

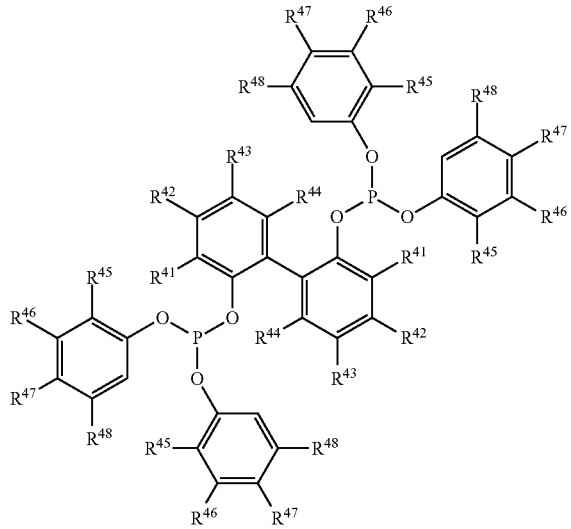

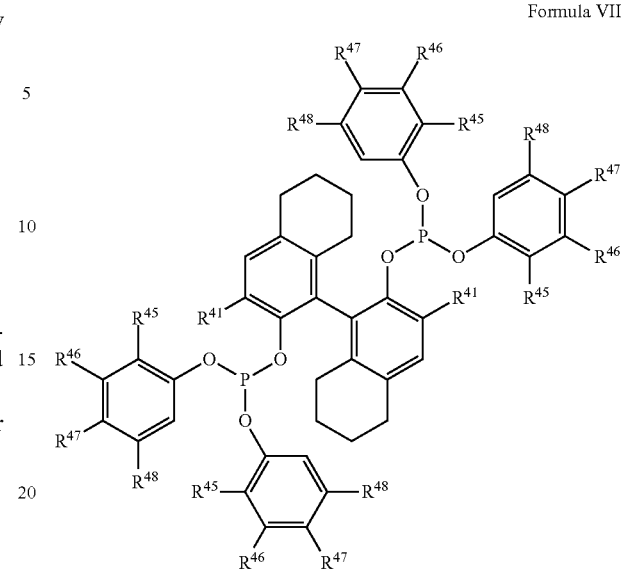

wherein, $R^{41}$ and $R^{45}$ are independently selected from the group consisting of $C_1$ to $C_5$ hydrocarbyl, and each of $R^{42}$, $R^{43}$, $R^{44}$, $R^{46}$, $R^{47}$ and $R^{48}$ is independently selected from the group consisting of H and $C_1$ to $C_4$ hydrocarbyl;

or wherein the phosphorus-containing ligand is a bidentate phosphite selected from the group consisting of Formula VII and VIII wherein, $R^{41}$ is methyl, ethyl, isopropyl or cyclopentyl;
$R^{42}$ is H or methyl;
$R^{43}$ is H or a $C_1$ to $C_4$ hydrocarbyl;
$R^{44}$ is H or methyl;
$R^{45}$ is methyl, ethyl or isopropyl; and
$R^{46}$, $R^{47}$ and $R^{48}$ are independently selected from the group consisting of H and $C_1$ to $C_4$ hydrocarbyl;

wherein the phosphorus-containing ligand is a bidentate phosphite selected from the group consisting of Formula VII and VIII wherein, $R^{41}$, $R^{44}$, and $R^{45}$ are methyl;
$R^{42}$, $R^{46}$, $R^{47}$ and $R^{48}$ are H; and
$R^{43}$ is a $C_1$ to $C_4$ hydrocarbyl;

or $R^{41}$ is isopropyl;
$R^{42}$ is H;
$R^{43}$ is a $C_1$ to $C_4$ hydrocarbyl;
$R^{44}$ is H or methyl;
$R^{45}$ is methyl or ethyl;
$R^{46}$ and $R^{48}$ are H or methyl; and
$R^{47}$ is H, methyl or tertiary-butyl;

wherein the phosphorus-containing ligand is a bidentate phosphite selected from the group consisting of Formula VII and VIII wherein, $R^{41}$ is isopropyl or cyclopentyl;
$R^{45}$ is methyl or isopropyl; and
$R^{46}$, $R^{47}$, and $R^{48}$ are H;

and wherein the phosphorus-containing ligand is a bidentate phosphite selected from the group consisting of Formula VII and VIII wherein, $R^{41}$ is isopropyl; $R^{42}$, $R^{46}$, and $R^{48}$ are H; and $R^{43}$, $R^{44}$, $R^{45}$, and $R^{47}$ are methyl.

Furthermore, when the phosphorus-containing ligand is a bidentate phosphite, the bidentate phosphite can be selected from the group consisting of Formula IX Formula IX

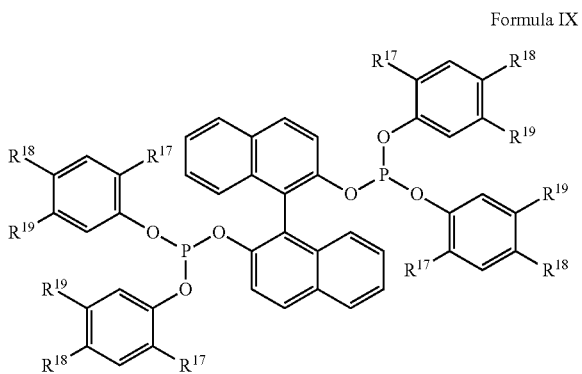

wherein $R^{17}$ is isopropyl, $R^{18}$ is hydrogen, and $R^{19}$ is methyl; and Formula X Formula X

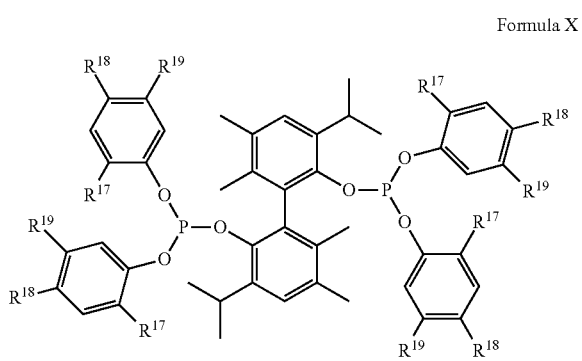

wherein $R^{17}$ is methyl, $R^{18}$ is methyl, and $R^{19}$ is hydrogen.

Additional bidentate ligands, ligand complexes, and methods of making the same, are disclosed in U.S. Pat. No. 6,171,996, herein incorporated by reference in its entirety.

In any preceding method including reacting the nickel-containing solid with a monodentate phosphorus-containing ligand, the reacting of the nickel-containing solid with the monodentate phosphorus-containing ligand can further include at least one halogenated catalyst including a phosphorus-halide bond selected from the group consisting of $PX_3$, $R^{17}PX_2$, $R^{18}OPX_2$, $[R^{19}][R^{20}]PX$, $[R^{21}][R^{22}O]PX$, and $[R^{23}O][R^{24}O]PX$; wherein $R^{17}$, $R^{18}$, $R^{19}$, $R^{20}$, $R^{21}$, $R^{22}$, $R^{23}$, and $R^{24}$ are independently selected from the group consisting of $C_1$ to $C_{18}$ hydrocarbyl radicals and each X is a halide independently selected from the group consisting of chloride, bromide, and iodide The bidentate phosphorus containing ligands can further include at least one Lewis acid promoter. The Lewis acid can be selected from the group consisting of inorganic or organometallic compounds that include an element selected from the group including scandium, titanium, vanadium, chromium, manganese, iron, cobalt, copper, zinc, boron, aluminum, yttrium, zirconium, niobium, molybdenum, cadmium, rhenium, lanthanum, europium, ytterbium, tantalum, samarium, and tin. For example, the at least one Lewis acid is selected from the group consisting of zinc chloride, ferrous chloride, or a combination of zinc chloride and ferrous chloride.

The reaction between the nickel-containing solid and the phosphorus-containing ligand can further include an organonitrile, such as a pentenenitrile. For example, the organonitrile can be selected from one or more members of the group consisting of 2-pentenenitrile, 3-pentenenitrile, 4-pentenenitrile, 2-methyl-3-butenenitrile, 2-methyl-2-bytenenitrile, adiponitrile, 2-methylglutaronitrile, and ethylsuccinonitrile.

Making the nickel complex or nickel complexes from the reaction of monodentate and bidentate ligands with the nickel-containing solids of this invention can be performed as described in U.S. Provisional Application No. 61/287,757 and the following Examples. For example, a 5 wt % solution of a bidentate phosphorus-containing ligand in pentenenitrile solvent further including a Lewis acid like $ZnCl_2$ (0.5 to 2.5 moles Lewis acid per mole bidentate phosphorus-containing ligand) is contacted with the nickel-containing solid of the invention (for example, 4.0 wt % nickel-containing solid). Temperatures between 60° C. and 80° C. give acceptable reaction rates. Sufficient agitation can be used to suspend the nickel-containing solid in this reaction mixture.

EXAMPLES

Definitions of Abbreviations:
ADN=adiponitrile; Aryl=unsubstituted or substituted aryl radical including 6 to 18 carbon atoms; BD=1,3-butadiene; hrs=hours; BNC=basic nickel carbonate; 2M3BN=2-methyl-3-butenenitrile; MGN=2-methylglutaronitrile; pentenenitrile or pentenenitriles=4PN, 3PN, 2PN, 2M3BN, and 2M2BN isomers unless specifically limited; 2PN=2-pentenenitrile including both c2PN and t2PN isomers unless specifically limited; 3PN=3-pentenenitrile including both c3PN and t3PN unless specifically limited; 4PN=4-pentenenitrile; ppm=parts per million by weight; wt %=% by weight.

Various aspects of the disclosed BNC compositions, nickel-containing solids, phosphorus-containing nickel metal complexes, and methods of making the same can be further understood in view of the following non-limiting examples. In the following paragraphs, all references are incorporated herein by reference.

Bidentate Phosphorus-Containing Ligand

Examples 1 to 13 use a bidentate phosphite ligand, Ligand A. Ligand A can be prepared by any suitable synthetic means known in the art. For example, 3,3'-diisopropyl-5,5',6,6'-tetramethyl-2,2'-biphenol can be prepared by the procedure disclosed in U.S. Published Patent Application No. 2003/0100802 in which 4-methylthymol can undergo oxidative coupling to the substituted biphenol in the presence of a copper chlorohydroxide-TMEDA complex (TMEDA is N,N,N',N'-tetramethylethylenediamine) and air. The phosphorochloridite of 2,4-xylenol, $[(CH_3)_2C_6H_3O]_2PCl$, can be prepared, for example, by the procedure disclosed in U.S. Published Patent Application No. 2004/0106815. To selectively form this phosphorochloridite, anhydrous triethylamine and 2,4-xylenol can be added separately and concurrently in a controlled manner to $PCl_3$ dissolved in an appropriate solvent under temperature-controlled conditions. The reaction of this phosphorochloridite with the 3,3'-diisopropyl-5,5',6,6'-tetramethyl-2,2'-biphenol to form the desired Ligand A can be performed, for example, according to the method disclosed in U.S. Pat. No. 6,069,267, herein incorporated by reference. The phosphorochloridite can be reacted with 3,3'-diisopropyl-5,5',6,6'-tetramethyl-2,2'-biphenol in the presence of an organic base to form Ligand A, which can be isolated according to techniques well known in the art, for example as also described in U.S. Pat. No. 6,069,267. Ligand A is an example of a compound of Formula I and the Ligand A solutions in 3PN solvent below do not contain any halogenated catalysts of U.S. Pat. No. 3,903,120.

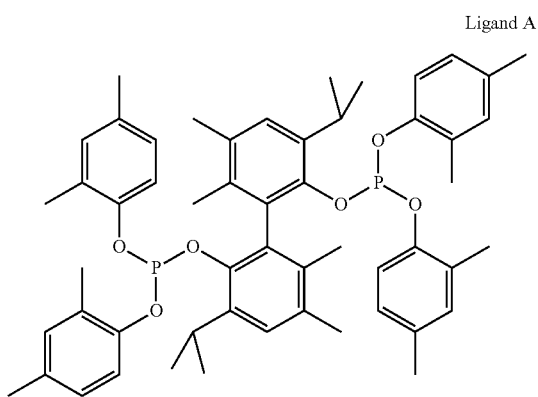

Ligand A

Example 16 uses a mixture of different monodentate phosphites, and Ligand B, that is derived from the reaction of a m-cresol/p-cresol/phenol mixture with $PCl_3$. Ligand B is an example of a compound of Formula II.

$$[m\text{-}(CH_3)C_6H_4O]_x[p\text{-}(CH_3)C_6H_4O]_y(C_6H_5O)_zP \qquad \text{Ligand B}$$

wherein x+y+z=3.

Example 1

A one molar $NiCl_2$ solution (250 mL, 0.25 mole $NiCl_2$) in water is charged to a 1 liter beaker then this solution is magnetically stirred with heating to 70° C. While maintaining this temperature, a precipitant solution including bicarbonate ions (25.2 gm of $NaHCO_3$ dissolved in 400 mL water, 0.30 mole $NaHCO_3$) is fed continuously into the beaker at a rate of 10 mL/min as the reaction mixture is sparged with added $CO_2$ gas at a rate of 100 mL/min. At the conclusion of the precipitant solution addition, the total moles of bicarbonate ions fed per mole of nickel ions charged is 1.2:1. This addition causes a solid product, a BNC composition including nickel, to precipitate from the reaction mixture. After all the precipitant solution is added, the flow of carbon dioxide gas to the reaction mixture is then terminated and the resulting reaction mixture slurry is then allowed to digest for 2 hours at 70° C. At the conclusion of this digestion period, this slurry is then filtered using a sintered glass filter and the solid filter cake is displacement washed with 200 mL water. The solid filter cake is then dried in a vacuum oven at 80° C. overnight while sweeping nitrogen through the vacuum oven.

Fifteen grams of the dried solid filter cake is then placed inside a reaction tube that can be heated within an electrical furnace located in a lab fume hood. Hydrogen gas flow to the reaction tube is then set at 0.2 liters/minute (about one atmosphere) with any hydrogen off-gas from the reaction tube flowing through a bubbler. The temperature of the tube furnace is then increased at a rate of 10° C./minute to a final temperature of 400° C., and then held for one hour at 400° C., after which the reaction tube is allowed to cool under hydrogen flow. After the reaction tube temperature falls below 50° C. the flow to the reaction tube is switched to nitrogen gas to purge the hydrogen from the reaction tube. Valves on the reaction tube are then closed to prevent exposure of the resulting nickel-containing solid, including nickel metal, to air, and the entire reaction tube is transferred to a nitrogen-filled dry box and the nickel-containing solid emptied into a bottle. This nickel-containing solid contains nickel metal as it is observed to be attracted to a magnet. Exposing these nickel-containing solids to air can reduce rates for the following reaction and/or cause the nickel-containing solids to burn in air to form nickel oxide.

Nickel complexes are also prepared in this nitrogen-filled dry box by placing 3.2 gm of this nickel-containing solid, 80 gm of a 5 wt % Ligand A solution in 3PN, and 0.50 gm of anhydrous $ZnCl_2$, into a bottle reactor that contained a magnetic stir bar. The nickel-containing solid is not soluble in this reaction mixture. With magnetic stirring, the reaction mixture is then heated rapidly to 80° C., and a filtered sample is withdrawn from this reaction mixture after 30 minutes and is found to contain 1460 ppm nickel, according to a UV-visible or LC analysis, as nickel complexes of Ligand A dissolved in the 3PN. For example, a calibrated absorption method that detects the soluble divalent nickel complex (Ligand A)Ni($\eta^3$-$C_4H_7$)C≡N—$ZnCl_2$ by the amount of absorption at a wavelength of 380 nanometers is used. This absorption method is calibrated against a LC analysis for total soluble nickel.

Examples 2 to 5

The general procedure of Example 1 is repeated in Examples 2 to 5, except that the total moles of bicarbonate ions fed per mole of nickel ions charged is varied from 1.6:1 to 2.0:1 by adjusting the amount of $NaHCO_3$ dissolved in the 400 mL water to prepare the precipitant solution. Results from the reaction of the resulting nickel-containing solids with the Ligand A solution and $ZnCl_2$ are provided in Table 1.

TABLE 1

Effect of the First Molar Ratio, Moles Bicarbonate Ions Fed/Mole Nickel Ions Charged, on the Reaction of the Resulting Nickel-Containing Solid with Ligand A and $ZnCl_2$ to Produce Nickel Complexes of Ligand A.

| Example | Precipitant Solution | | Moles HCO3 Ions Fed/Mole Ni Ions Charged | ppm Ni* |
| --- | --- | --- | --- | --- |
| | gm NaHCO3 | mole NaHCO3 | | |
| 1 | 25.2 | 0.30 | 1.2 | 1460 |
| 2 | 33.6 | 0.40 | 1.6 | 1390 |
| 3 | 37.8 | 0.45 | 1.8 | 1060 |
| 4 | 39.3 | 0.47 | 1.9 | 823 |
| 5 | 42.0 | 0.50 | 2.0 | 92 |

*As nickel complexes of Ligand A dissolved in the 3PN.

Examples 1 through 5 illustrate that as the amount of bicarbonate ions fed is increased relative to the nickel ions charged, there is a decline in the reactivity of the resulting nickel-containing solid with a phosphorus-containing ligand to form soluble nickel complexes. That is, greater amounts of nickel complexes are formed when this first molar ratio, moles bicarbonate ions fed/mole nickel ions charged, is between 0.0:1 and 2.0:1.

Example 6

Example 2 is repeated except in the absence of sparging $CO_2$ gas through the reaction mixture during the feeding of the sodium bicarbonate solution to the 1 liter beaker containing the nickel ions. As shown in Table 2, greater amounts of nickel complexes are formed from the reaction of the resulting nickel-containing solid with the Ligand A solution and $ZnCl_2$ when the solid product precipitates in the presence of added $CO_2$ gas.

TABLE 2

Effect of the Presence of Added $CO_2$ Gas During the Precipitation of the Solid Product on the Reaction of the Resulting Nickel-Containing Solid with Ligand A and $ZnCl_2$ to Produce Nickel Complexes of Ligand A.

| Example | Precipitant Solution | | Moles HCO3 Ions Fed/Mole Ni | ppm Ni* |
|---|---|---|---|---|
| | gm NaHCO3 | mole NaHCO3 | Ions Charged | |
| 2 | 33.6 | 0.40 | 1.6 | 1390 |
| 6 | 33.6 | 0.40 | 1.6 | 965 |

*As nickel complexes of Ligand A dissolved in the 3PN.

Examples 7 and 8

Example 2 is repeated except that temperatures of the heated $NiCl_2$ solution, reaction mixture during continuous feeding of the precipitant solution to the 1 liter beaker, and digestion period are 50° C. for Example 7 and 90° C. for Example 8. In comparison to Example 2 (see Table 3), greater amounts of nickel complexes are formed from the reaction of the resulting nickel-containing solid with the Ligand A solution and $ZnCl_2$ when the solid product precipitates at 70° C. rather than 50° C. or 90° C.

TABLE 3

Effect of Precipitation Temperature on the Reaction of the Resulting Nickel-Containing Solid with Ligand A and $ZnCl_2$ to Produce Nickel Complexes of Ligand A.

| Example | Heated $NiCl_2$ Solution | Reaction Mixture | Digestion Period | ppm Ni* |
|---|---|---|---|---|
| 2 | 70° C. | 70° C. | 70° C. | 1390 |
| 7 | 50° C. | 50° C. | 50° C. | 845 |
| 8 | 90° C. | 90° C. | 90° C. | 850 |

*As nickel complexes of Ligand A dissolved in the 3PN according to an analysis.

Example 9

Example 2 is repeated except substituting $NiSO_4$ for $NiCl_2$. That is, continuously feeding the precipitant solution of Example 2 to a 1 molar $NiSO_4$ solution (250 mL, 0.25 mole $NiSO_4$) in water at 70° C. Similar to solid product precipitated from $NiCl_2$, equivalent amounts of nickel complexes are formed (1465 ppm nickel) after 30 minutes from the reaction of the resulting nickel-containing solid with the Ligand A solution and $ZnCl_2$ when the solid product precipitates from the $NiSO_4$ solution.

Example 10

A 1 molar $NiSO_4$ solution (250 mL, 0.25 mole $NiSO_4$) in water is charged to a 1 liter beaker then this solution is magnetically stirred with heating to 70° C. While maintaining this temperature, a precipitant solution including carbonate ions (21.2 gm of $Na_2CO_3$ dissolved in 400 mL water, 0.20 mole $Na_2CO_3$) is fed continuously into the beaker at a rate of 10 mL/min but no $CO_2$ gas is sparged into the reaction mixture. At the conclusion of the precipitant solution addition, the total moles of carbonate ions fed per mole of nickel ions charged is 0.8. This addition also causes a solid product to precipitate from the reaction mixture. After all the precipitant solution is added, the resulting reaction mixture slurry is then allowed to digest for 2 hours at 70° C. At the conclusion of this digestion period, this slurry is then filtered using a sintered glass filter, and the solid filter cake is displacement washed with 200 mL water. The solid filter cake is then dried in a vacuum oven at 80° C. while sweeping nitrogen through the vacuum oven overnight.

Fifteen grams of the dried solid filter cake is reduced with hydrogen flow at elevated temperatures as described in Example 1. Nickel complexes are also prepared as described in Example 1. A filtered sample is withdrawn from the reaction mixture in the bottle reactor after 30 minutes and is found to contain 1420 ppm nickel, according to a UV-Visible or LC analysis, as nickel complexes of Ligand A dissolved in the 3PN.

Examples 11 to 13

The general procedure of Example 10 is repeated in Examples 11 to 13. The difference being that the total moles of carbonate ions fed per mole of nickel ions charged is varied from 1.0:1 to 1.6:1 by adjusting the amount of $Na_2CO_3$ dissolved in the 400 mL water to prepare the precipitant solution. Results from the reaction of the resulting nickel-containing solids with the Ligand A solution and $ZnCl_2$ are provided in Table 4.

TABLE 4

Effect of the Second Molar Ratio, Moles Carbonate Ions Fed/Mole Nickel Ions Charged, on the Reaction of the Resulting Nickel-Containing Solid with Ligand A and $ZnCl_2$ to Produce Nickel Complexes of Ligand A.

| Example | Precipitant Solution | | Moles CO3 Ions Fed/Mole Ni | ppm Ni* |
|---|---|---|---|---|
| | gm Na2CO3 | mole Na2CO3 | Ions Charged | |
| 10 | 21.2 | 0.20 | 0.8 | 1420 |
| 11 | 26.5 | 0.25 | 1.0 | 1340 |
| 12 | 31.8 | 0.30 | 1.2 | 1065 |
| 13 | 42.0 | 0.40 | 1.6 | 0 |

*As nickel complexes of Ligand A dissolved in the 3PN.

Examples 10 through 13 illustrate that the reactivity of the resulting nickel-containing solid with a phosphorus-containing ligand to form soluble nickel complexes can decline as the amount of carbonate ions fed is increased relative to the nickel ions charged. That is, greater amounts of nickel complexes are formed when this second molar ratio, moles carbonate ions fed/mole nickel ions charged, is between 0.0 and 1.6.

Example 14

Example 5 is repeated except that the order of addition is reversed for the solid precipitation reaction in the 1 liter beaker. That is, the 1 molar $NiCl_2$ solution is added to the precipitant solution to precipitate a solid product. After digestion, filtration, displacement washing, drying, reducing with hydrogen gas in the reactor tube at 400° C., followed by reacting the resulting nickel-containing solid with the Ligand A solution in 3PN and $ZnCl_2$, the filtered sample withdrawn from the reaction mixture is found to contain 0 ppm nickel as nickel complexes of Ligand A dissolved in the 3PN.

Example 15

At a constant precipitation temperature, the weight of the dried solid filter cake is also a function of the total moles of bicarbonate (Examples 1 to 9, Table 5) or carbonate ions (Examples 10 to 13, Table 6) fed per mole of nickel ions charged.

TABLE 5

Effect of the First Molar Ratio, Moles Bicarbonate Ions Fed/Mole
Nickel Ions Charged, on the Weight of the Dried Solid Filter Cake and
Reaction of the Resulting Nickel-Containing Solid with Ligand A and ZnCl$_2$ to
Produce Nickel Complexes of Ligand A.

| | Example | | | | | | | | | |
|---|---|---|---|---|---|---|---|---|---|---|
| | 1 | 2 | 6 | 7 | 8 | 9 | 3 | 4 | 5 | 14 |
| Precipiating Temperature | 70° C. | 70° C. | 70° C. | 50° C. | 90° C. | 70° C. | 70° C. | 70° C. | 70° C. | 70° C. |
| Moles HCO3 Ions Fed/Mole Ni Ions Charged | 1.2 | 1.6 | 1.6 | 1.6 | 1.6 | 1.6 | 1.8 | 1.9 | 2.0 | 2.0 |
| gm Dried Solid Filter Cake | 16.2 | 21.70 | 22.1 | 22.3 | 15.9 | 23.5 | 24.2 | 26.8 | 27.6 | 26.2 |
| ppm Ni* | 1460 | 1390 | 965 | 845 | 850 | 1465 | 1060 | 823 | 92 | 0 |

TABLE 6

Effect of the Second Molar Ratio, Moles Carbonate Ions Fed/Mole
Nickel Ions Charged, on the Weight of the Dried Solid Filter Cake
and Reaction of the Resulting Nickel-Containing Solid with Ligand A and
ZnCl$_2$ to Produce Nickel Complexes of Ligand A.

| Example | 10 | 11 | 12 | 13 |
|---|---|---|---|---|
| Moles CO3 Ions Fed/Mole Ni Ions Charged | 0.8 | 1.00 | 1.2 | 1.6 |
| gm Dried Solid Filter Cake | 23.6 | 26.70 | 28.7 | 32.7 |
| ppm Ni* | 1420 | 1340 | 1065 | 0 |

*As nickel complexes of Ligand A dissolved in the 3PN.

Also, it is generally observed that times required for the filtration of the precipitated solid product and displacement wash of the solid filter cake, as described in Examples 1 to 14, are greater when the solid product is precipitated using carbonate ions in comparison to using bicarbonate ions. For example at equivalent filtration conditions, the filtration time is 14 minutes and the displacement wash time is 40 minutes for the solid product of Example 11 that is precipitated with carbonate ions. But for the solid product precipitated with bicarbonate ions, the filtration time and displacement wash time can both be less than 1 minute each.

Example 16

The nickel-containing solids of Examples 1 to 13 are reacted with the monodentate phosphite Ligand B in 3PN solvent to form nickel complexes, including zero-valent nickel and Ligand B, in the absence of a Lewis acid such as ZnCl$_2$.

Example 17

ZnCl$_2$ is at least partially separated from the nickel complex of Examples 1 to 12 then the nickel complex of Ligand A contacts BD and HC≡N in a reaction zone. A catalyst forms to produce 3PN, 2M3BN, or a combination thereof. The same nickel complexes also react with 2M3BN to produce 3PN.

Nickel complexes of Ligand B of Example 16 contact HC≡N and BD in a reaction zone. A catalyst forms to produce 3PN, 2M3BN, or a combination thereof. The same nickel complexes also react with 2M3BN to produce 3PN.

In the presence of a Lewis acid promoter, like ZnCl$_2$, the soluble nickel complexes of Ligand A from bottle reactors of Examples 1 to 12 contact HC≡N and 3PN in a reaction zone. A catalyst forms converting greater than 90% of the 3PN to dinitriles including ADN, MGN, and ESN, with an ADN distribution of 95-96%. The ADN distribution equals 100%*wt % ADN/(wt % ADN+wt % MGN+wt % ESN), as determined by gas chromatography (GC).

In the presence of a Lewis acid promoter, like ZnCl$_2$, the soluble nickel complexes of Ligand A from bottle reactors of Examples 1 to 12 contact HC≡N and 2PN in a reaction zone. A catalyst forms converting a portion of the 2PN to 3PN, 4PN, and ADN.

In the presence of a Lewis acid promoter, like ZnCl$_2$, triphenylboron, or compounds of the chemical formula [Ni(C$_4$H$_7$C≡N)$_6$][(C$_6$H$_5$)$_3$BC≡NB(C$_6$H$_5$)$_3$]$_2$ as disclosed in U.S. Pat. No. 4,749,801, the nickel complexes of Example 16 contact HC≡N and 3PN in a reaction zone. A catalyst forms converting 3PN to dinitriles including ADN, MGN, and ESN, wherein ADN is the major dinitrile product.

The invention has been described above with reference to the various aspects of the disclosed nickel(II) compositions, basic nickel carbonates, and methods of making the same. Obvious modifications and alterations will occur to others upon reading and understanding the proceeding detailed description. It is intended that the invention be construed as including all such modifications and alterations insofar as they come within the scope of the claims.

What is claimed is:

1. A method of making a nickel complex of a phosphorus-containing ligand comprising:
   reacting a nickel metal with a phosphorus-containing ligand, wherein the nickel metal is provided by reducing a nickel(II) composition formed according to a process comprising the steps of
   (i) contacting, while agitating, a nickel(II) salt dissolved in water with a precipitant selected from the group consisting of bicarbonate salt, carbonate salt, and a combination thereof, to form a reaction mixture comprising an water phase and a precipitate comprising the nickel(II) composition; and
   (ii) controlling the contacting rate so that the water phase has a pH between about 4.0 and about 7.5.

2. The method of claim 1, wherein controlling further comprises controlling an amount of the precipitant added to the nickel(II) salt dissolved in water.

3. The method of claim 1, wherein the precipitant comprises a bicarbonate salt and wherein the contacting rate is controlled such that a first mole ratio is between about 0.5 and about 2.0, wherein the first mole ratio is the total moles of bicarbonate salt contacted divided by the total moles of nickel (II) salt in the reaction mixture.

4. The method of claim 1, wherein the precipitant comprises a carbonate salt and wherein the contacting rate is controlled such that a second mole ratio is between about 0.5 and about 1.6, wherein the second mole ratio is the total moles of carbonate salt contacted with the nickel (II) salt dissolved in water divided by the total moles of nickel(II) salt in the reaction mixture.

5. The method of claim 1, wherein the contacting is carried out within a precipitation reactor by feeding a precipitant solution into a precipitation reactor which contains the nickel (II) salt dissolved in water to form the reaction mixture,
wherein the feeding of the precipitant solution is controlled:
(a). such that a first mole ratio is between about 0.5 and about 2.0, wherein ttie first mole ratio is the total moles of bicarbonate salt divided by the total moles of nickel (II) salt charged into the precipitation reactor; or
(b). such that a second mole ratio is between about 0.5 and about 1.6, wherein the second mole ratio is the total moles of carbonate salt contacted with the nickel(II) salt dissolved in water divided by the total moles of nickel (II) salt charged into the precipitation reactor.

6. The method of claim 1, further comprising maintaining a reaction mixture temperature between about 25° C. and about 90° C.

7. The method of claim 1, further comprising adding carbon dioxide to the nickel(II) salt dissolved in water or the reaction mixture.

8. The method of claim 1, further comprising digesting the precipitate by heating the reaction mixture between about 50° C. and about 90° C. for a time period of about 0.5 hour to about 24 hours.

9. The method of claim 3, further comprising precipitating the nickel(II) composition from the reaction mixture utilizing at least two precipitating conditions selected from the group consisting of precipitating conditions (1), (2), and (3):
(1) a reaction mixture temperature between about 60° C. and about 80° C.;
(2) addition of carbon dioxide to the reaction mixture; and
(3) a first mole ratio between about 0.5 and about 1.6.

10. The method of claim 4, further comprising precipitating the nickel(II) composition from the reaction mixture utilizing at least two precipitating conditions selected from the group consisting of conditions (4), (5), and (6):
(4) a reaction mixture temperature between about 60° C. and about 80° C.;
(5) addition of carbon dioxide to the reaction mixture; and
(6) a second mole ratio between about 0.5 and about 1.2.

11. The method of claim 9 wherein conditions (1), (2), and (3) are utilized.

12. The method of claim 10, wherein conditions (4), (5), and (6) are utilized.

13. The method of claim 3, wherein the first mole ratio is between about 1.0 and about 1.9 at a conclusion of the contacting.

14. The method of claim 4, wherein the second mole ratio is between about 0.8 and about 1.4 at a conclusion of the contacting.

15. The method of claim 1, further comprising separating the precipitated nickel(II) composition from the reaction mixture followed by at least one processing step selected from the group consisting of:
(a) washing the precipitated nickel(II) composition with water; and
(b) at least partially drying the precipitated nickel(II) composition.

16. The method of claim 15, wherein at least a portion of the washed precipitated nickel(II) composition from processing step (a), at least a portion of the at least partially dried precipitated nickel(II) composition from processing step (b), or at least a portion of the washed and at least partially dried precipitated nickel(II) composition from processing steps (a) and (b) is reduced to form the nickel metal.

17. The method of claim 1 wherein a carbon to nickel mole ratio for the nickel(II) composition is between about 0 and about 0.5.

18. The method of claim 1 wherein the phosphorus-containing ligand is a monodentate phosphite, monodentate phosphonite, monodentate phosphinite, monodentate phosphine, bidentate phosphite, bidentate phosphonite, bidentate phosphinite, bidentate phosphine, mixed bidentate ligand, or any combination thereof;
wherein the mixed bidentate ligand is selected from the group consisting of a phosphite-phosphonite, a phosphite-phosphinite, a phosphite-phosphine, a phosphonite-phosphinite, a phosphonite-phosphine, and a phosphinite-phosphine.

19. The method of claim 18 wherein the phosphorus-containing ligand is a bidentate phosphite, bidentate phosphonite, bidentate phosphinite, bidentate phosphine, mixed bidentate ligand, or any combination of such members; and reacting the nickel metal with the phosphorus-containing ligand further comprises addition of a Lewis acid.

20. A method to make a nickel complex of a phosphorus-containing ligand, wherein a phosphorus-containing ligand reacts with nickel metal to make the nickel complex of the phosphorus-containing ligand; characterized in that the nickel metal is produced by reducing a nickel(II) composition and the nickel(II) composition produces carbon dioxide when heated.

\* \* \* \* \*